United States Patent [19]

Katz et al.

[11] Patent Number: 4,712,565

[45] Date of Patent: Dec. 15, 1987

[54] METHOD AND APPARATUS FOR EVALUATING OF ARTIFICIAL HEART VALVES

[75] Inventors: Hart V. Katz, Willowdale, Canada; Gerald A. Kien, Tower Lakes, Ill.

[73] Assignee: International Acoustics Incorporated, Palatine, Ill.

[21] Appl. No.: 923,576

[22] Filed: Oct. 27, 1986

[51] Int. Cl.$^4$ ............................................... A61B 5/02
[52] U.S. Cl. ................................................... 128/715
[58] Field of Search ................................ 128/695–697, 128/701, 714, 715, 773; 364/415, 417

[56] References Cited

U.S. PATENT DOCUMENTS

| | | | |
|---|---|---|---|
| 3,052,756 | 9/1962 | Seven et al. | 128/715 |
| 4,428,381 | 1/1984 | Hepp | 128/715 |
| 4,458,693 | 7/1984 | Badzinski et al. | 128/715 |
| 4,498,188 | 2/1985 | Hofer | 128/715 |

OTHER PUBLICATIONS

"Sound Spectroanalytic Diagnosis of Malfunctioning Prosthetic Heart Valve", J. Exp. Med., 1977, Kagawa et al.

*Primary Examiner*—Max Hindenburg
*Attorney, Agent, or Firm*—Irwin C. Alter

[57] ABSTRACT

A method and apparatus for evaluating of implanted artificial (mechanical or bioprosthetic) heart valves includes a microprocessor responsive to a series of digital signals for processing a portion of the series of digital signals corresponding to valve sounds in a phonocardiogram. A deconvolution algorithm is provided to transform the portion of the series of digital signals into an impact history signal which characterizes the motion of the occluding elements and an impulse response signal. A microprocessor is used to transform the impulse response into a power spectrum signal and to calculate ring down times therefrom which characterize the physical structure of the valve cage. A recorder is provided for graphically portraying the extent and nature of degradation and deterioration of the heart valve. Such a printed graphic record of the impact history signal can then be precisely evaluated and a period-to-period comparison can be made with an earlier recorded impact history signal.

16 Claims, 4 Drawing Figures

DECONVOLUTION ALGORITHM

METHOD AND APPARATUS FOR EVALUATING OF ARTIFICIAL HEART VALVES

BACKGROUND OF THE INVENTION

This invention relates generally to medical diagnostic methods and devices in the field of cardiology and more particularly, it relates to a method and apparatus for evaluating of artificial (mechanical or bioprosthetic) heart valves which is based upon analysis of acoustic signals generated by the artificial valves. The present invention is accomplished by a signal processing technique sometimes referred to as deconvolution analysis which is done without invading the body of the patient.

Various non-invasive methods and apparatuses of the prior art have been attempted by utilizing imaging techniques for evaluation of the integrity of prosthetic mechanical heart valves. Other prior art arrangements have attempted to use invasive hemodynamic studies where there has been clinical evidence of a valve failure of a more advanced nature. However, all of the prior art methods and apparatuses suffer from the disadvantage of being unable to detect or identify early structural or environmental changes associated with evolving valve degeneration or malfunction.

It would therefore be desirable to provide a method and apparatus for evaluating implanted artificial heart valves that utilize a deconvolution technique to extract and display intrinsic information from heart sounds or phonocardiogram which occur as the valve cycles in systole and diastole, thereby permitting an early identification of changes associated with valve malfunction.

SUMMARY OF THE INVENTION

Accordingly, it is a general object of the present invention to provide an improved method and apparatus for evaluating of implanted artificial heart valves which is relatively simple and economical to manufacture and assemble, but yet overcomes the disadvantages of the prior art devices.

It is an object of the present invention to provide a method and apparatus for evaluating artificial heart valves which utilize a deconvolution technique to extract and display intrinsic information from heart sounds, thereby permitting an early identification of changes associated with valve malfunction.

It is another object of the present invention to provide an apparatus for non-invasive evaluation of artificial heart valves which includes a deconvolution algorithm for transforming a portion of a series of digital signals corresponding to valve sounds into an impact history signal for characterizing the motion of the occluding elements of the valve.

It is still another object of the present invention to provide an apparatus for non-invasive evaluation of artificial heart valves which includes a microprocessor for processing a portion of a series of digital signals corresponding to valve sounds and a deconvolution algorithm for transforming the portion of the series of digital signals into a deconvoluted impact history signal for characterizing the motion of the occluding elements of the valve.

It is yet still another object of the present invention to provide an apparatus for non-invasive evaluation of artificial heart valves which includes a microprocessor for calculating an impulse response signal, for calculating a power spectrum signal and for calculating ring down times from the power spectrum signal in which the power spectrum and ring down times characterize the physical structure of the valve cage.

In accordance with these aims and objectives, the present invention is concerned with the provision of an apparatus for non-invasive evaluation of implanted artificial heart valves which includes a transducer for converting heart sounds into electrical signals corresponding to a phonocardiogram. An amplifier is used to amplify the electrical signals and for generating amplified electrical signals. There is provided a filter for filtering the amplified electrical signals and for generating filtered electrical signals. An analog-to-digital converter is provided for converting the filtered electrical signals into a series of digital signals. A microprocessor responsive to the series of digital signals is provided to process a portion of the series of digital signals corresponding to valves sounds in the phonocardiogram. A deconvolution algorithm is used to transform the portion of the series of digital signals into an impact history signal for characterizing the motion of the occluding elements of the valve and an impulse response signal. A microprocessor is used to transform the impulse response signal into a power spectrum signal and to calculate ring down times therefrom which characterize the physical structure of the valve cage. A recorder is provided to record graphically the digital output signals corresponding to the impact history, impulse response and power spectrum.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein.

DESCRIPTION OF THE PREFERRED EMBODIMENT

Figure 1:
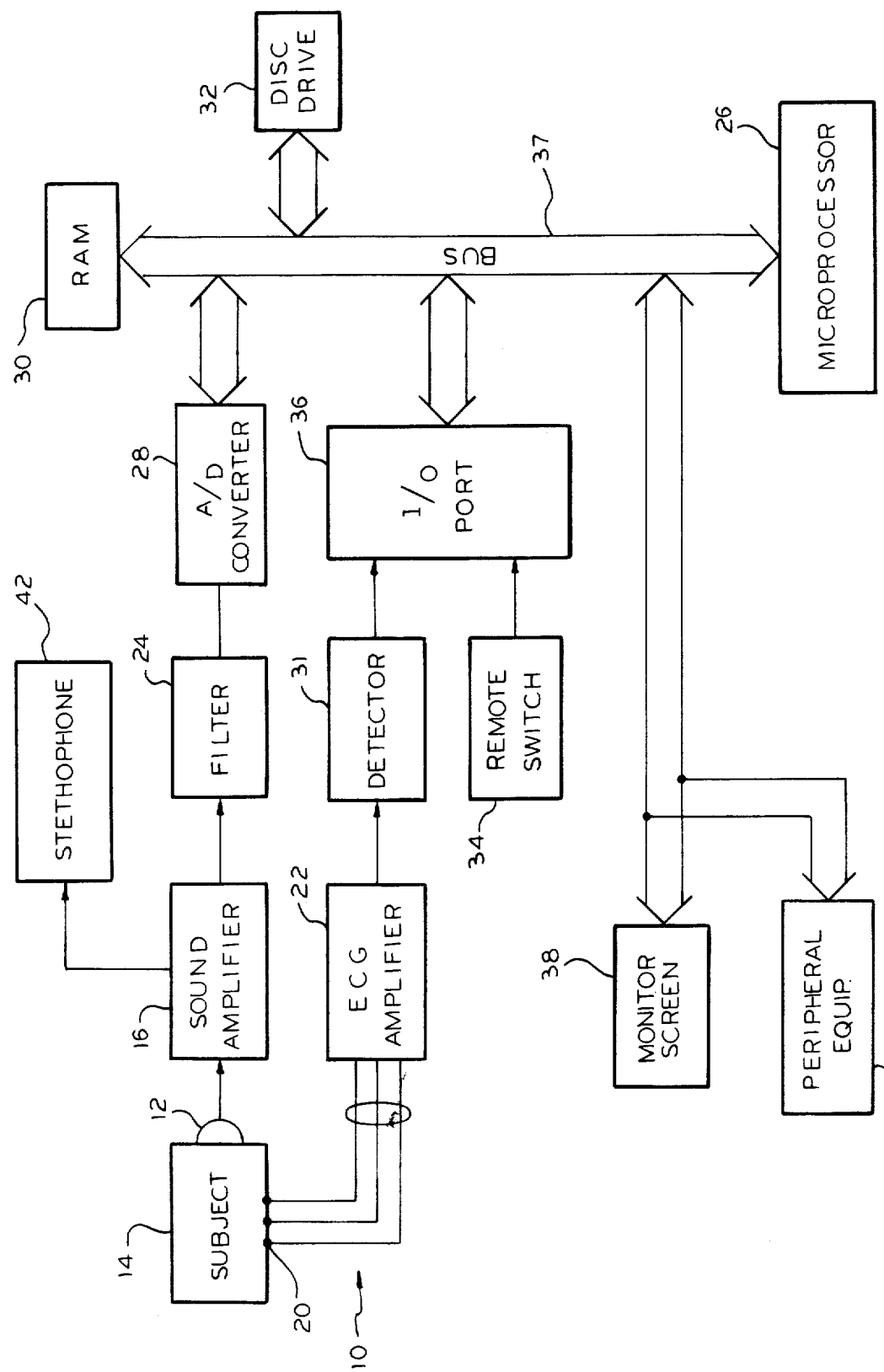
FIG. 1 is a block diagram of the method and apparatus for evaluating of artificial heart valves, utilizing the principles of the present invention.

Referring now in detail to the drawings, there is shown in FIG. 1 a block diagram of the method and apparatus 10 of the present invention for evaluating implanted artificial (mechanical or bioprosthetic) heart valves which utilize a deconvolution technique. The apparatus 10 includes a transducer 12 which is placed on the chest of a subject or patient 14 under investigation for receiving a phonocardiogram representing sound waves. The transducer 12 consists of an accelerometer microphone which functions as an input device for converting the sound waves from the patient with a prosthetic mechanical or bioprosthetic heart valve into electrical signals and applying the signals to a sound amplifier 16. If it is desired to obtain the position of the R-wave of the electrocardiogram (ECG) along with the phonocardiogram, a three-wire ECG cable 18 may be connected via electrodes 20 to the skin surface of the patient. In this case, the other end of the cable 18 is connected to an ECG amplifier 22.

The sound amplifier 16 amplifies the weak transducer signals and applies the amplified signals to a low-pass filter 24. The filter 24 comprises an anti-aliasing filter which is used to eliminate aliasing problems encountered with analog-to-digital conversion. The output of the filter 24 is connected to an analog-to-digital (A/D) converter 28. The A/D converter 28 samples the output of the sound amplifier 16 at a predetermined sampling frequency and produces a series of digital signals representative of the output waveform of the sound amplifier 16. A sampling frequency of 8 KHz is considered adequate for the purposes of this invention. This series of digital signals is then stored in a random-access memory 30 by the microprocessor 26 which operates under the control of the program installed from a diskette inserted in the disk drive 32. In addition, the microprocessor 26 is capable of being turned on and off by a remote switch 34 through the digital I/O port 36 for remotely starting the analysis.

An output bus 37 carries either the digitized phonocardiogram signals or the output of the mathematical analysis and digital control signals to a monitor screen or display unit 38 for visual display of the phonocardiogram analysis. The digital output signals from the bus 37 may also be fed to other digital periphery output equipment 40 such as a recorder, graphic printer, X-Y plotter and the like for generating appropriate output data for analysis i.e., a printed graphic record for precise evaluation of current conditions and period-to-period comparison with earlier graphs to show changes over time.

The output of the ECG amplifier 22 provides an ECG signal which is fed to the input of an ECG R-wave detector 31. The R-wave detector 31 generates an R-wave control signal which is fed to the microprocessor 26 via the I/O port 36. Thus, the microprocessor can cause a mark, time coincident with the R-wave for display on the monitor screen 38 or the peripheral equipment 40. The sound amplifier 16 has a second output which is connected to a stethophone 42 wherein the cardiac auscultatory sounds may be heard as they are seen on the monitor screen 38 by a physician.

Figure 2:
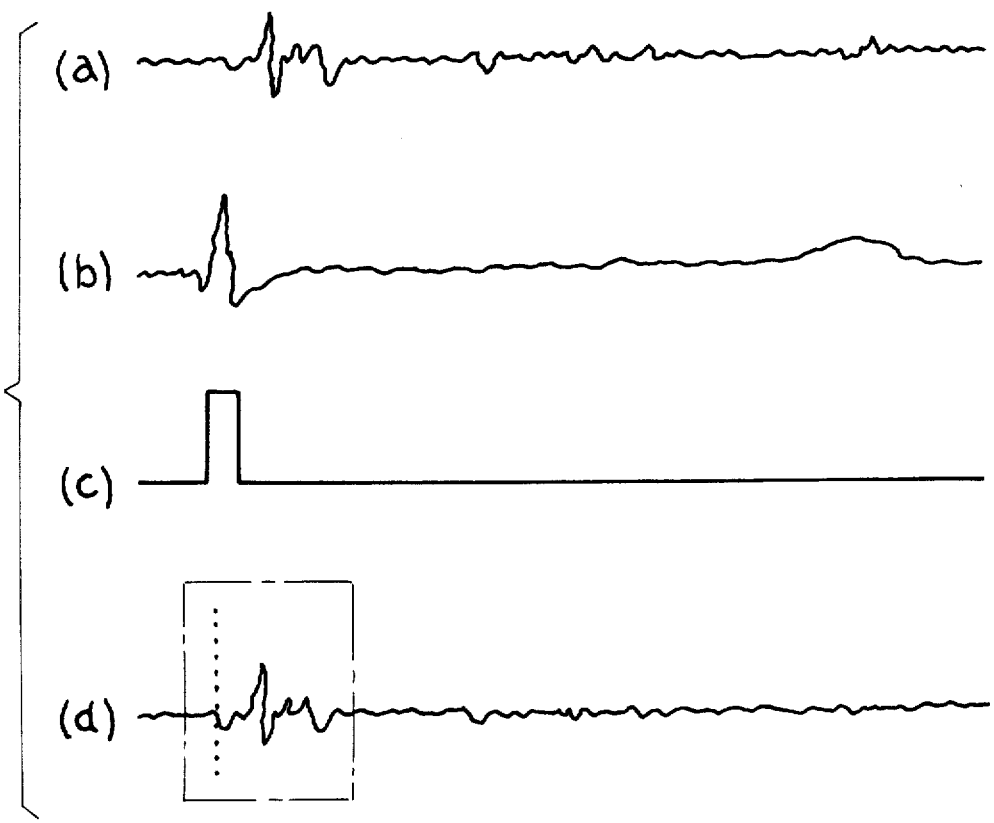
FIGS. 2(a)–2(d) depict graphically various waveforms useful in understanding the operation of the invention.

In FIGS. 2(a)-2(d), there are shown various waveforms at particular points in the apparatus 10 which are useful in understanding the operation of the present invention. The waveform A in FIG. 2(a) represent the electrical output signals of sound amplifier 16 which correspond to the cardiac auscultatory signal or the phonocardiogram of the cardiac cycle in response to a complex stream of impact events. These impact events vary in intensity and in their temporal relationship. As can be seen, the phonocardiogram is a complex composite waveform caused by a sum of individual time-varying impulsive forces. It is not possible to manually and-/or visually dissect the complex waveform into its individual components signals in order to determine the nature of the stream of impact forces which may have caused this acoustic response pattern.

However, information of the impact forces is present in the acoustic signal. The deconvolution algorithm, which is an integral feature of the present invention, provides the deconvolution technique for extracting such impact events and for quantifying the same. Specifically, the deconvolution technique allows a physician to see the temporal sequence of impacts of the valve's occluding elements (i.e., disc, leaflets, or ball) as they strike the valve cage, and it characterizes the valve cage, itself, by quantifying the parameter of its acoustic response to the impacting forces.

Waveform B in FIG. 2(b) represents the ECG signal at the output of the ECG amplifier 22 while waveform C in FIG. 2(c) represents the R-wave control signal at the output of the R-wave detector 31. Waveform D in FIG. 2(d) is a windowed portion of the phonocardiogram shown in the waveform A which corresponds to the mechanical valve sound. The waveform D shown in FIG. 2(d) has been enlarged and is illustrated in FIG. 3(a). The microprocessor 26 uses a microprogram or deconvolution algorithm transferred from the diskette in the disk drive 32 to operate on the windowed signal, which has been digitized by the A/D converter 28, so as to obtain an impact history which is depicted in FIG. 3(b). An impulse response of the valve is shown in FIG. 3(c) which is defined as the acoustic signal generated by the valve cage when there is only a single impact (unit impulse) of the occluding element of the valve on a valve cage surface. Thus, the complete acoustic signal of the closing valve consists of the temporal summation of the impulse response acording to the pattern reflected in the impact history.

Figure 3:
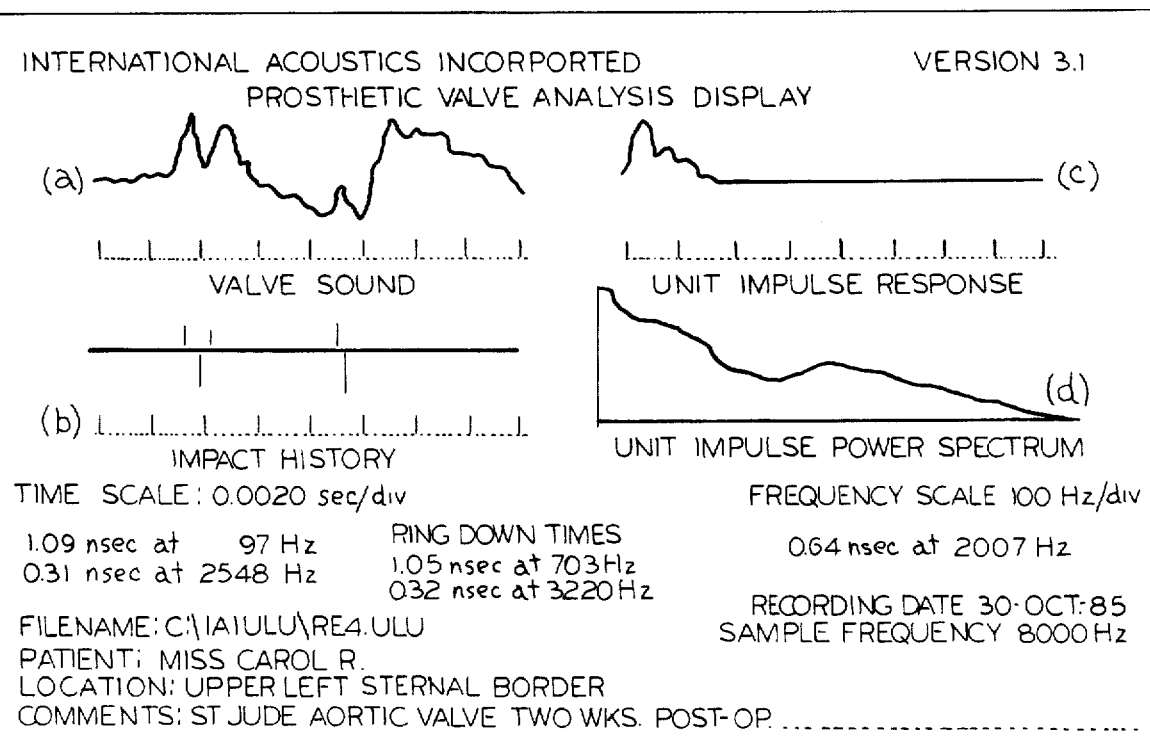
FIGS. 3(a)–3(d) depict additional waveforms which are useful in understanding the operation of the invention.

In this example, the impact history illustrated in FIG. 3(b) reveals four major impact lines and a number of minor impact lines. Such an impact pattern may be anticipated for a bi-leaflet type valve wherein each of the two occluding elements will independently strike the valve cage in their closing cycle. The double impact lines may reflect multiple surface contact components of each leaflet, or may reflect a longer duration circumferential surface contact of the leaflets being represented as multiple impact events. In FIG. 3(d) there is depicted a graphical portrayal of the magnitude of the power spectrum of the impulse response shown in FIG. 3(c). By quantifying the parameters (ring down times shown in numbers at the bottom of FIG. 3) of the acoustic response of the valve to an impact, there is provided a characterization of the physical structure of the valve cage system.

In use, the impact history, impulse response and power spectrum waveforms and ring down time calculations are initially obtained from the valve after it is implanted in the patient and are recorded on the peripheral equipment 40. At a subsequent time to the initial recording, these same waveforms and calculations are obtained from the valve and are compared with the initial recordings to evaluate if a change has occurred in the valve. Structural failure of the valve of a noncritical nature, or clot or fibrin formation on an occluding surface or occluding element would result in changes in the impact history. Also, changes in the impact history would result due to tissue encroachment or any impedance to motion due to positional constraints. Further, any change in its structure due to failure of a valve component member or due to attachment of tissue would be reflected as a change in the power spectrum of the valve, i.e., its characteristic frequencies, the relative power at those frequencies and their component ring-down times. Accordingly, it can thus be seen by the utilization of these waveforms and comparing them with earlier recorded ones, the physician would be able to detect and identify the early changes in the evolution of valve degeneration.

Figure 4:
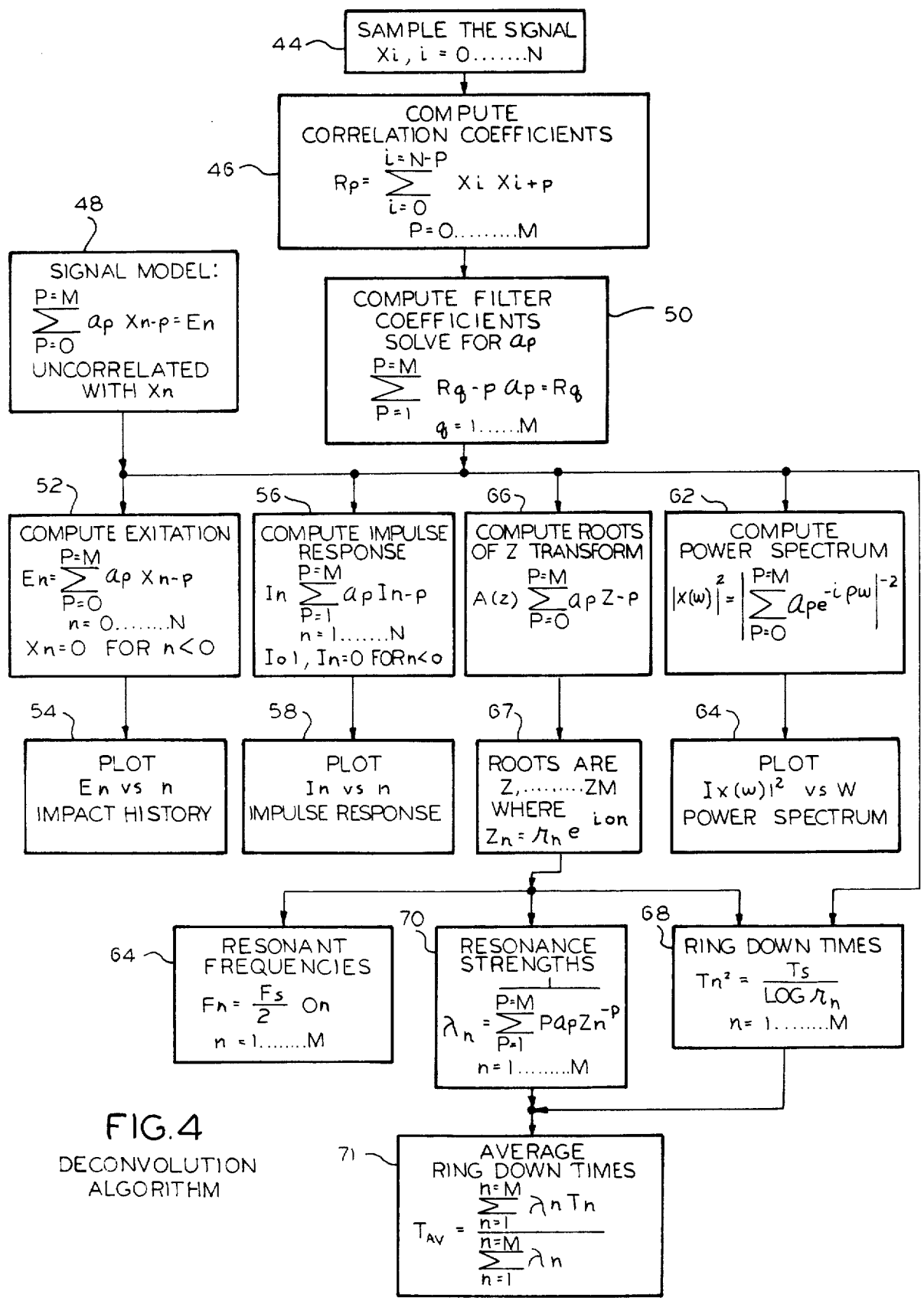
FIG. 4 is a flow chart of the deconvolution algorithm depicted in FIG. 1 illustrating how the waveforms of the impact history, impact response and power spectrum are obtained from the heart sound.

FIG. 4 is a flow chart of the deconvolution algorithm illustrating how the impact history, impact response and power spectrum waveforms and ring down time calculations are obtained from the heart sound. In particular, the phonocardiogram representing sound wave signals from the transducer 12, which are passed through the sound amplifier 16 and the low-pass filter 24, are sampled by the analog-to-digital converter 28 so as to produce a series of digital signals. The sampled digital signals can be expressed as a plurality of values X(i) for i=0 to N, where N is equal to the number of samples taken as shown in 44. A general linear model 48, for the heart valve can be expressed mathematically as follows:

$$E(n) = \sum_{p=0}^{p=M} A(p)X(n-p) \text{ for } n = 0 \text{ to } N \quad (1)$$

where

E(n) = sampled value of the external forces impacting on the valve cage

X(i) = sampled acoustical signal generated by the vibrating valve cage

A(p), p=1 to M are empirical constants which characterize the valve cage.

Throughout the following description it is assumed that the acoustical signal is sampled at a sampling frequency of $F_s$ samples per second.

Correlation coefficients R(p) are computed in 46 from the digital signal values X(i) as follows:

$$R(p) = \sum_{i=0}^{i=N-p} X(i)X(i+p) \text{ for } p = 0 \text{ to } M \quad (2)$$

where

X(i) = portion of digital signals corresponding to the windowed signal of FIG. 3(a)

X(i) = 0 for i out of the windowed area M = order of model

Next, the values of the constants A(p) are found by solving the equation as is shown in 50. The values of the constants A(p) are then combined with the sampled digital signal values X(i) determined from 44 so as to provide an estimate for the impact history as illustrated in 52. This is expressed mathematically as follows:

$$E(n) = \sum_{p=0}^{p=M} A(p)X(n-p) \quad (3)$$

This above equation (3) is then plotted (FIG. 3(b)) as a function of n in order to obtain what is called the impact history which characterizes the motion of the occluding elements of the valve as shown in 54.

The valve impulse response is defined as the response to a unit impulse. Equation (3) of 52 can be solved for values for I(n) 56, as follows:

$$I(n) = \sum_{p=1}^{p=M} A(p)I(n-p) \quad (4)$$

The above equation (4) is then plotted (FIG. 3(c)) as a function of n in order to display graphically the impulse response as illustrated in 58.

The power spectrum of the sampled digital signal values X(i) is:

$$X(w)^2 = \frac{|E(w)|^2}{|A(w)|^2} \quad (5)$$

If En is a unit impulse, and $$E(w)^2 = 1 \quad (6)$$

$$X(w)^2 = \frac{1}{|A(w)|^2} \quad (7)$$

Equation (7) is the power spectrum of the impulse response.

By using the constants A(p) determined in 50, the term A(w) can be computed as follows:

$$A(w) = \sum_{p=0}^{p=M} A(p)e^{-iPw} \quad (8)$$

Thus, the power spectrum of X(n) of equation (5) can be expressed as:

$$X(w)^2 = \frac{1}{\left|\sum_{p=0}^{p=M} A(p)e^{-iPw}\right|^2} \quad (9)$$

Equation (9) is achieved by 62 and X(w)² is plotted (FIG. 3(d)) as a function of w in 64.

The ring down time is defined as the decay time or "half life" of the power spectrum resonances. The Z transform is computed as:

$$A(z) = \sum_{p=0}^{p=M} A(p)Z^{-p} \quad (10)$$

The roots of the Z transform satisfy $$A(z) = 0 \quad (11)$$

The roots of the equation (11) are determined by 66 and 67 and the decay times calculated as a function of the magnitude of these roots. In particular, the $i^{th}$ decay time $T_i$ is related to the $i^{th}$ root $z_i$ by:

$$T_i = \frac{1}{F_s \text{LOG}_{10}|Z_i|} \quad (12)$$

These ring down times are shown by 68. The resonant frequencies are proportional to the phase of the roots as calculated in 69. The resonant frequencies and ring down times characterize the physical structure of the valve cage. As the valve cage deteriorates, the ring down times will change.

The resonance strengths are calculated in 70 and the average ring down time is calculated in 71. The average ring down time is displayed as a number.

In view of the foregoing, it is not believed necessary to describe the software under which the microprocessor 26 is operated. It is believed that those skilled in the art will have no difficulty in providing an appropriate program.

From the foregoing detailed description, it can thus be seen that the present invention provides an improved method and apparatus for evaluating of artificial heart valves which is based upon analysis of acoustic signals generated by the artificial valves. Further, there is provided a microprocessor program for processing a portion of a series of digital signals corresponding to valve sounds and a deconvolution algorithm for transforming the portion of the series of digital signals into an impact history signal for characterizing the motion of the occluding elements of the valve and a power spectrum signal and calculated ring down times for characterizing the physical structure of the valve cage. These signals can then be compared with similar ones taken earlier so as to effect an early identification of changes associated with valve malfunction.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

What is claimed is:

1. An apparatus for non-invasive evaluation of implanted artificial heart valves, comprising:
   transducer means for converting heart sounds into electrical signals corresponding to a phonocardiogram;
   amplifying means for amplifying the electrical signals and for generating amplified electrical signals;
   means for filtering said amplified electrical signals and for generating filtered electrical signals;
   means for converting said filtered electrical signals into a series of digital signals;
   microprocessor means responsive to said series of digital signals for processing a portion of said series of digital signals corresponding to valve sounds in the phonocardiogram;
   a deconvolution algorithm for transforming said portion of said series of digital signals into an impact history signal to characterize the occluding elements of the valve;
   means for converting said impact history signal into a digital output signal; and
   means for recording graphically said digital output signal.

2. An apparatus as claimed in claim 1, wherein said digital output signal representative of said impact history signal is presented for comparison with an earlier impact history signal taken from a patient so as to detect early deterioration of the valve shown by changes in the impact history.

3. An apparatus as claimed in claim 1, wherein said microprocessor means is responsive to said portion of said series of digital signals for calculating an impulse response signal.

4. An apparatus as claimed in claim 3, wherein said microprocessor means includes means dor transforming said impulse response signals into a power spectrum signal for calculating ring down times therefrom which characterize the physical structure of the valve cage.

5. An apparatus as claimed in claim 4, wherein said power spectrum signal and ring down times are compared with an earlier power spectrum signal and earlier ring down times taken from the patient so as to determine early deterioration of the heart valve shown by changes in the power spectrum signal and ring down times.

6. An apparatus as claimed in claim 1, wherein said transducer means comprises an accelerometer microphone.

7. An apparatus as claimed in claim 1, wherein said amplifier means comprises a sound amplifier.

8. An apparatus as claimed in claim 1, wherein said means for converting said filtered electrical signals into a series of digital signals comprises an analog-to-digital converter.

9. An apparatus as claimed in claim 1, wherein said means for converting said impact history signal into a digital output signal comprises a microprocessor.

10. An apparatus as claimed in claim 9, wherein said transducer means comprises an accelerometer microphone.

11. An apparatus as claimed in claim 10, further comprising detector means responsive to an ECG signal for generating an R-wave control signal.

12. A method for non-invasive evaluation of implanted artificial heart valves, comprising the steps of:
   converting heart sounds into electrical signals corresponding to a phonocardiogram;
   amplifying the electrical signals to generate amplified electrical signals;
   filtering said amplified electrical signals to generate filtered electrical signals;
   converting said filtered electrical signals into a series of digital signals;
   extracting a portion of said series of digital signals corresponding to valve sounds in the phonocardiogram;
   transforming said portion of said series of digital signals into an impact history signal to characterize the occluding elements of the valve; and
   recording graphically said impact history signal.

13. A method as claimed in claim 12, further comprising the step of presenting said impact history signal for comparison with an earlier impact history signal taken from a patient so as to detect earlier deterioration of the valve shown by changes in the impact history.

14. A method as claimed in claim 12, further comprising the step of calculating an impulse response signal in response to said portion of said series of digital signals.

15. A method as claimed in claim 14, further comprising the step of transforming said impulse response signals into a power spectrum signal and for calculating ring down times therefrom which characterize the physical structure of the valve cage.

16. A method as claimed in claim 15, further comprising the step of presenting said power spectrum signal and ring down times for comparison with an earlier power spectrum signal and earlier ring down times taken from the patient so as to determine early deterioration of the heart valve shown by changes in the power spectrum signal and ring down times.

* * * * *

UNITED STATES PATENT AND TRADEMARK OFFICE
CERTIFICATE OF CORRECTION

PATENT NO. : 4,712,565
DATED : December 15, 1987
INVENTOR(S) : Hart V. Katz and Gerald A. Kien It is certified that error appears in the above-identified patent and that said Letters Patent are hereby corrected as shown below:

Col. 5, line 63    Equation (4) should read as follows in its entirety:

$$I(n) = \sum_{p=1}^{p=M} A(p)I(n-p) \qquad (4)$$

$$I(o) = 1$$

$$I(n) = o \quad n < o$$

Signed and Sealed this

Seventh Day of June, 1988

Attest:

DONALD J. QUIGG

Attesting Officer    Commissioner of Patents and Trademarks